United States Patent [19]

Schultz

[11] Patent Number: 4,687,329

[45] Date of Patent: Aug. 18, 1987

[54] SPECTROPHOTOMETER

[75] Inventor: Steven G. Schultz, Winthrop Harbor, Ill.

[73] Assignee: Abbott Laboratories, North Chicago, Ill.

[21] Appl. No.: 941,247

[22] Filed: Dec. 12, 1986

Related U.S. Application Data

[63] Continuation of Ser. No. 714,312, Mar. 21, 1985.

[51] Int. Cl.[4] ............................. G01J 3/02; G01J 3/36
[52] U.S. Cl. .................................. 356/328; 250/226; 350/317; 357/30
[58] Field of Search ............... 356/308, 326, 328, 331, 356/332, 334, 414, 416, 417, 419; 250/226; 350/311, 317, 318; 357/30 H, 30 L; 358/43, 44

[56] References Cited

U.S. PATENT DOCUMENTS

| | | | |
|---|---|---|---|
| 3,869,212 | 3/1975 | Burcher et al. | 356/419 |
| 3,973,118 | 8/1976 | LaMontagne | 356/416 |
| 4,003,635 | 1/1977 | Ottersberg et al. | 350/318 |

FOREIGN PATENT DOCUMENTS

| | | | |
|---|---|---|---|
| 0121404 | 10/1984 | European Pat. Off. | 356/328 |
| 0165085 | 12/1980 | Japan | 358/43 |
| 0087007 | 7/1981 | Japan | 350/317 |
| 0078003 | 5/1982 | Japan | 350/311 |
| 0105024 | 6/1983 | Japan | 356/331 |
| 0105025 | 6/1983 | Japan | 356/331 |
| 0114684 | 7/1983 | Japan | 358/44 |
| 0172536 | 10/1983 | Japan | 356/328 |
| 0178324 | 10/1984 | Japan | 356/328 |
| 0043985 | 3/1985 | Japan | 350/311 |
| 2096352 | 10/1982 | United Kingdom | 356/417 |

OTHER PUBLICATIONS

*Electric Product Design,* Jul. 1981, p. 9.

Primary Examiner—F. L. Evans
Attorney, Agent, or Firm—Martin L. Katz; Donald L. Corneglio

[57] ABSTRACT

An improved spectrophotometer, especially suitable for use in centrifugal analysis instrumentation, is disclosed. The spectrophotometer is improved by including therein a detector comprising a photodiode array assembly having a photodiode array, a spectral filter assembly situated substantially parallel thereto and in the path of incident light and means for attenuating stray light which would otherwise impinge on each of the photodiodes of the array.

3 Claims, 4 Drawing Figures

SPECTROPHOTOMETER

This is a continuation of application Ser. No. 714,312, filed Mar. 21, 1985.

BACKGROUND OF THE INVENTION

1. Field of the Invention

The invention relates to a spectrophotometer. More particularly, it relates to an improved spectrophotometer especially useful for optical analysis of samples in a centrifugal analyzer.

2. Background Art

Spectrophotometers are well known in the art, and comprise various main components. The light source usually comprises one or two continuous-emission lamps, e.g., halogen, deuterium, mercury arc and/or xenon. Prism or grating devices are used for the dispersion. The detectors are generally photomultipliers, or silicon photodiodes. The numerous kinds of available components and the various possible structures can be combined in numerous ways to construct a spectrophotometer having desired characteristics for a particular intended use.

The disadvantages of known spectrophotometers are mainly due to the light source and the monochromator used. Particularly in spectrophotometers used in centrifugal analyzers, it is desirable to use a light source such as a flash lamp in order to enable high speed absorbance measurements. Accordingly, although the tungsten-halogen lamp is undoubtedly the most frequently-used source for applications in the visible spectrum, it has the following well-known disadvantages:

(a) very weak emission of ultraviolet light;
(b) very great variation of light intensity in the useful spectrum; the intensity of light at 290 nm is about 900 times less than at 700 nm;
(c) the proportion of interfering light is considerable, which means that expensive blocking filters need to be used;
(d) the system for compensating variations in light intensity with wavelength must have a wide dynamic range;
(e) the service life is relatively short;
(f) the light output is relatively low;
(g) the dissipated power is considerable; and
(h) the electric supply means for the lamp is relatively heavy and bulky.

In order to alleviate the disadvantages with the aforementioned kind of lamp, light can be obtained from lamps producing different kinds of electric (flash) discharges, e.g. xenon, mercury or argon lamps. Xenon lamps have the most uniform spectrum, and their light efficiency is much greater than that of tungsten. However, the lamps are usually supplied for higher power than 100 W, and are very difficult to cool. Also, the lamp supply and mounting means are very voluminous and expensive.

The grating monochromator is a preferred method of continuously varying the wavelength. However, the proportion of interfering light resulting from the associated lamp and monochromator must be very low, e.g., less than $1 \times 10^{-4}$, if it is desired to make measurements having a low linearity error (e.g. lower than 1.5% up to an attenuation of 1000 times (corresponding to an absorbance of 3)). To obtain performance of this kind, double-grating monochromators are ordinarily used, since single-grating monochromators have too high a proportion of interfering light. However, double-grating mmonochromators are expensive, bulky and take a relatively long time to align.

U.S. Pat. No. 3,810,696 discloses a spectrophotometer comprising a flash tube and an interference filter or a monochromator to produce two light beams, the first of which travels through a sample for analysis and the second of which reaches a detector which delivers a reference signal corresponding to the intensity of the second beam. U.S. Pat. No. 4,241,998 discloses a spectrophotometer intended in particular for the optical analysis of samples in a centrifugal analyzer. The spectrophotometer comprises a flash tube, a stabilizing optical device for deriving a light beam having a constant spatial distribution from each flash from the flash tube, a grating monochromator for dispersing the light delivered by the stabilizing device and for delivering a beam of filtered light, an optical element for dividing the filtered beam to produce two beams, the first of which travels through a sample for analysis and the second of which reaches a detector which delivers a reference signal corresponding to the intensity of the second beam, and a second detector placed to receive the beam emerging from the sample.

SUMMARY OF THE INVENTION

The present invention provides an improvement in a spectrophotometer of the type previously described, which overcomes or alleviates many of the problems with such conventional instruments. In particular, the invention provides a novel photodiode array assembly as a detector, which is especially suitable for use in an optical system of a small absorbance, multi-wavelength spectrophotometer. A typical application of such a spectrophotometer is in an automated clinical analyzer, such as those commonly used in medical laboratories. The critical nature of medical analysis requires a detection system to determine various substances of clinical interest in biological specimens, such as blood serum, urine, spinal fluid and the like, which is capable of a high degree of sensitivity. This sensitivity is frustrated by small sample size and high absorbance levels associated with a biological sample. Accordingly, the present invention enables an increase of sensitivity at the photodiode surface, by specifically controling the components of light impacting on individual photodiodes of the detector assembly, without resort to double-gratings or other relatively complex and expensive apparatus of the prior art.

In a preferred embodiment, an improved spectrophotometer of the invention comprises:

a flash lamp;

a grating monochromator for dispersing the light delivered by the flash lamp and for delivering a beam of filtered light which travles through a sample for analysis; and a detector situated to receive the beam emerging from the sample. The improvement of the invention involves the detector comprising a photodiode array assembly including:

(a) a plurality of individual photodiodes situated in a first plane;

(b) a plurality of individual spectral filters situated substantially parallel to the first plane and adjacent to the plurality of photodiodes such that light passing through each of the individual spectral filters will impinge upon only one of the individual photodiodes; and (c) means for attenuating stray light, the means being situated substantially parallel to the first plane and adjacent the plurality of individual spectral filters such that the means is located above each of the individual photodiodes, said attenuating means being capable of determining the spectral bandpass and the central wavelength of the light impinging on the individual photodiodes.

DETAILED DESCRIPTION OF THE INVENTION

Figure 1:
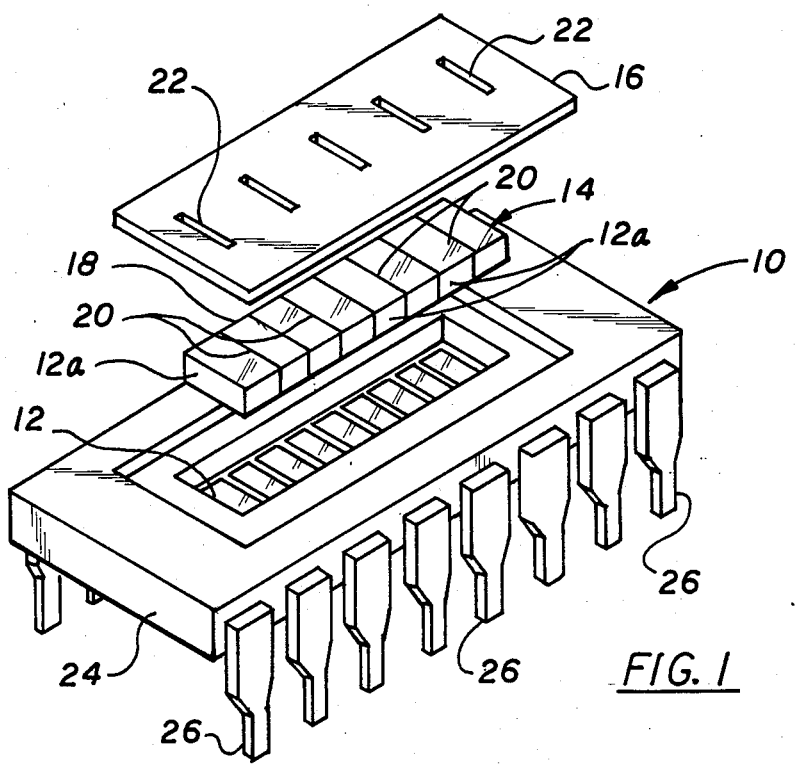
FIG. 1 is an exploded view in perspective showing components of a preferred optical detector useful in an improved spectrophotometer according to the present invention.

The present invention provides an improvement in a spectrophotometer which is especially suitable for use in a centrifugal clinical chemical analyzer comprising a rotor rotating at high speed, e.g., approximately 1800 rpm, and bearing small volume samples and/or reagents for analyzing such samples. Such a spectrophotometer generally will ideally have the following features:

(1) ability to measure absorbance of liquid samples deposited in analysis cells while rotating the cells at approximately 1800 rpm;

(2) brief duration of measurement of multiple samples on the rotor, i.e. in less than about 350 milliseconds;

(3) time available per measurement of less than about 5 microseconds;

(4) measurement of small volumes of liquid samples, i.e., on the order of 200 microliters;

(5) continuous selection of wavelengths, between about 340 and 640 nm;

(6) a bandwidth of about 8 nm;

(7) a wide range of measurable absorbance, i.e., from 0.0 to 3.0.

(8) have a relatively small size so as, for example, to fit into a laboratory bench top, or desk top analyzer;

(9) have no moving parts to greatly improve reliability; and

(10) have a minimum number of optical elements to be aligned, thus improving manufacturability and reliability.

The foregoing features are particularly important in automatic instruments in order to make up the considerable differences in absorbance between normal cases and pathological cases of samples of biological material under examination—e.g., between a lypaemic serum and a normal serum. An instrument having the foregoing characteristics is described in co-pending U.S. patent applications Ser. Nos. 606,785, 606,786, and 606,787, filed May 3, 1984, the disclosures of which are incorporated herein by reference.

In addition, the centrifugal analysis instrument which is improved with the present invention enables reproducibility of measurements compatible with the requirements for enzyme reactions. This refers to the reproducibility of measurements of absorbance on a single sample. This is particularly important in the case of kinetic methods. In these methods the variation in absorbance is slow, i.e. the measurements can be speeded up if reproducibility is good. In these methods also, the absorbance level is sometimes quite high (1.7-2.2). Thus, reproducibility must be excellent over a wide range of absorbance, a feature achieved by the present improvements.

Also, according to the instant invention excellent linearity between absorbance and concentration over a wide range of absorbance is achieved. This linearity simplifies the use of the instrument, in that a calibration curve is not needed. Linearity is difficult to obtain at high absorbance, specifically in the ultraviolet, and depends on the purity of the monochromatic light, i.e. on the proportion of interfering light, which is defined by the ratio of (a) the intensity of residual light emitted outside the selected spectral band to (b) the intensity of light inside the selected spectral band.

Furthermore, the improvements of the present invention, in order to reduce the bulk and cost of conventional spectrophotometers, utilize for the detector a photodiode array associated with conventional electronics.

The aforementioned photometric performance in a centrifugal analyzer, if it is to be achieved during a relatively short measuring time, creates special technical difficulties relating to the required signal/noise ratio and to obtaining a light beam having the required spectral purity for ultimate interpretation by the electronics of the instrument. Since it is ordinarily desired to make reproducible measurements with a maximum signal attenuation of about 1000 times through the sample, it is usually necessary for the signal/noise ratio to be at least $2 \times 10^{-5}$ at zero absorbance. Since the measurement time is very short (less than 5 microseconds) an amplifier having a wide pass band is needed, which makes it difficult to obtain the desired signal/noise ratio since, as is known, the noise increases with the width of the amplifier pass-band. The effect of this noise is considerable compared with the effect of noise in conventional spectrophotometers, in which the influence of noise on the measured results can be reduced by integrating the measured signal over one or more seconds. The problem of obtaining an adequate signal/noise ratio is made even more difficult because it is usually desired to use silicone photodiodes; the association of a photodiode with an amplifier is noisier than a photomultiplier operating at a weak signal level. This applies more particularly to wavelengths below 400 nm for measurements of high absorbance values ($A = 3$), since silicone photodiodes have a lower sensitivity than photomultipliers in this part of the spectrum.

Largely conventional analog-to-digital conversion electronic circuitry is used to convert current signals from the detector into digital information signals readable by associated microprocessor controlled circuitry.

In order to obtain the photometric characteristics described hereinbefore, the light beam supplied by the monochromator must have very high spectral purity, in order to avoid the well-known problems of nonlinearity due to interfering light and bandwidth effects. There are certain difficulties in obtaining a light beam having the spectral purity required for photometric purposes, if the cost and bulk of the spectrophotometer are to be simultaneously reduced. For these purposes, according to the invention, the proportion of interfering light is reduced to a value of approximately $1 \times 10^{-4}$ at a wavelength of 340 nm, using a detector assembly comprising a photodiode array, a multiwavelength spectral filter assembly between the photodiode array and the light source and means for attenuating stray light from the source prior to its impinging upon the spectral filter assembly.

Figure 2:
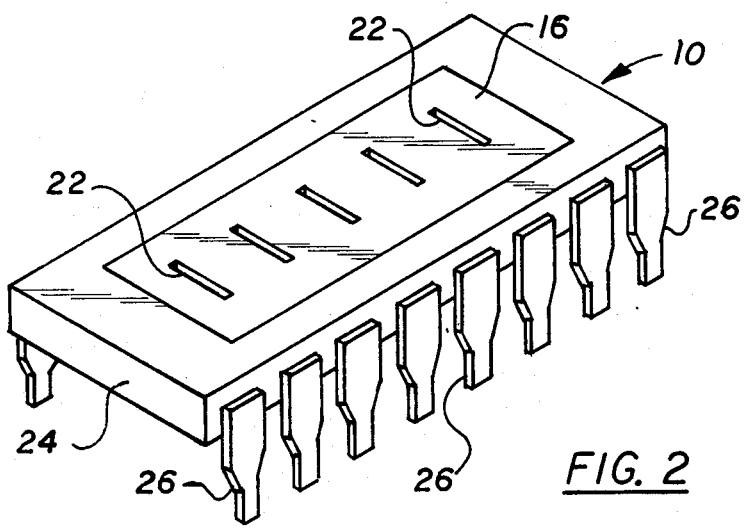
FIG. 2 is a perspective view of the detector shown in FIG. 1, but illustrating the detector in its fully-assembled condition.
Figure 3:
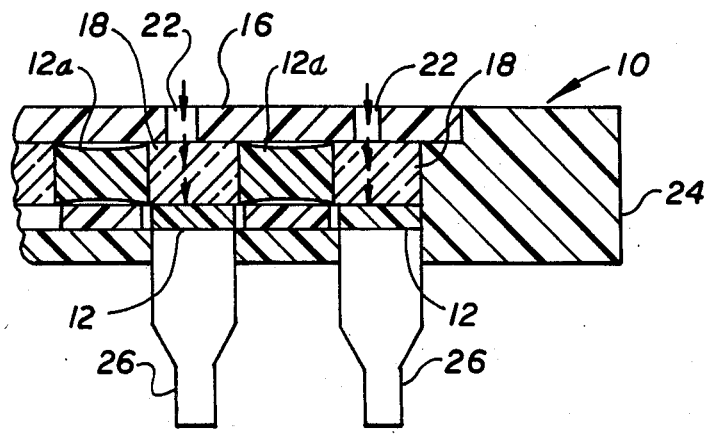
FIG. 3 is an enlarged, partial cross sectional view of the fully-assembled detector shown in FIG. 2, illustrating details of construction thereof.

Referring now to the drawings, and with particular reference to FIGS. 1 through 3, a preferred photodiode array detector assembly in accordance with the invention is shown generally at 10. The assembly 10 essentially comprises a photodiode array 12, a spectral filter assembly 14 and a means to attenuate stray light 16. The spectral filter assembly 14 comprises a plurality of optical grade glass filters 18 which are individually chosen for their pre-selected transmittance characteristics depending on the wavelength of light it is desired to have measured by the individual photodiodes of the array 12 which are below each of the filters. The filters 18 are assembled such that the four edges (indicated at 20) of each individual filter which are normal to the array 12 are surrounded by an optically opaque, poorly light-transmissive material 12a, such as a black epoxy. The opaque material 12a effectively shields the sides of each of the optical filters 18 from light not incident to the chosen surfaces of each filter. The opaque material 12a, in this preferred embodiment, also holds together the individual filters 18 in a desired planar configuration. The filter assembly 14, as shown, is mounted in a plane substantially parallel to the photodiode array 12 and in the path of incident light from a light source such that each individual one of the filters 18 is optically associated with a corresponding photodiode of the array 12. The means for attenuating stray light 16 that originates external to the spectral filter assembly 14, but which is not blocked by the opaque material shielding the side portion of each of the optical filters, in a preferred embodiment of the invention, comprises a "mask", of a suitable substance such as flat-black anodized metal, having a plurality of narrow slits therein which are located above the centerline of the surface area of each photodiode of the array 12. The stray light attenuating means 16 is, as shown, mounted in a plane substantially parallel to that of the filter assembly 14 and overlays the surfaces of the filters 18 thereof. The light attenuating means 16 also determines the central wavelength of light which impinges on the individual photodiodes of the array 12 by virtue of its lateral position in the focused spectrum of light. The width of slits 22 in means 16 furthermore functions to determine, to a more or less extent, the bandpass of the spectrophotometer. The slit width of slits 22 of means 16 also helps to normalize signal differences resulting from efficiency variations as a function of wavelength (e.g., caused by the source, spectrum grating efficiency, photodiode efficiency, and transmittance of filter assembly 14).

In the preferred fabrication of the detector assembly 10, the photodiode array 12, filter assembly 14 and light attenuating means 16 are mounted, as shown in FIGS. 1 and 2, in a suitable base 24 which includes a plurality of electrically conductive metal contacts 26 for electrical connection, when the assembly 10 is in use, to largely conventional electronic circuitry which, as well known to those skilled in the art, is capable of receiving and converting output signals produced by the photodiode array 12 in response to the intensities of light impinging thereupon. In a particular case the conversion can be, for example, to a digital readout corresponding to the absorbance of light by a constituent of a sample of biological material under analysis. The contacts 26 are secured in the base 24, which can be made of a ceramic, phenolic or other suitable commercially available dielectric material, in a well known manner so that they are in electrical connection with the output portion of individual ones of the photodiodes of the array 12 (FIG. 3).

As best shown in FIG. 3, the individual filters 18 are positioned in contact with the photodiodes of the array 12, and the stray light attenuating means 16 is positioned over the array 12 in contact with the filters 18, such that the slits 22 thereof create an incident light path (as shown by the arrows) through the means 16, the filters 18 and to the diodes of the array 12. However, the opaque material 12a functions effectively to block any of the incident light, after entering a particular slit 22, from impinging upon any of the photodiodes of the array 12 which are not intentionally positioned directly beneath that slit. Such a preferred construction in accordance with the invention has been found experimentally to reduce "cross talk", or the effect of such incident light impinging upon an unintended photodiode, to a value of less than about 60 ppm.

Figure 4:
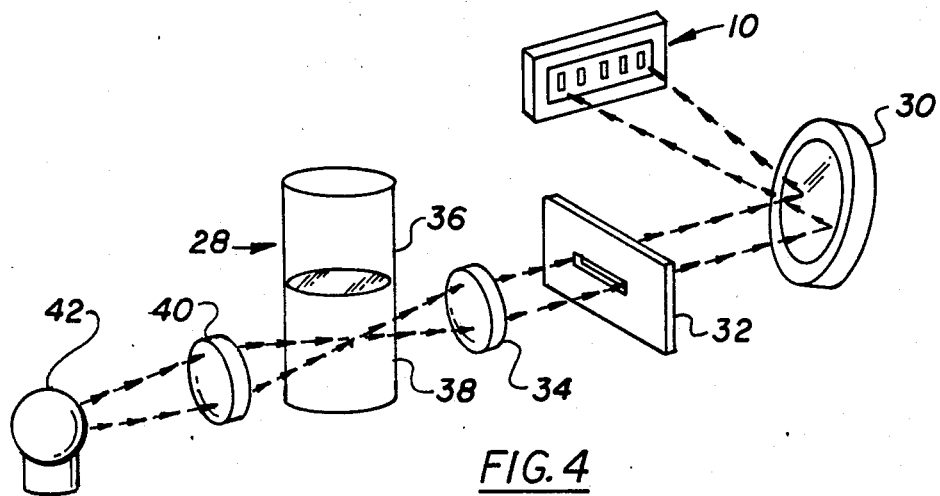
FIG. 4 is a schematic diagram in perspective, showing the detector of FIGS. 1-3 and other components of an improved optical system of a spectrophotometer which incorporates the concepts of the invention.

Referring now to FIG. 4 of the drawings, a preferred embodiment of an improved optical system of a spectrophotometer of the type aforedescribed, which incorporates the concepts of the present invention, is indicated generally at 28. The system 28, it is to be appreciated, is of largely conventional design except for the inclusion of the detector assembly 10. Furthermore, it is to be appreciated that the system 28 can be incorporated into a conventional optical housing, but preferably is enclosed in a cast aluminum housing machined such that a first surface of the concave diffraction grating is located at a critical distance from both the entrance slit of the housing, through which light emerging from the sample passes, and the detector assembly. This configuration enables manufacturing ease as well as tight optical focusing. In addition, all machining of the casting is done from the same end to improve tolerances. The system 28 comprises the detector assembly 10, a concave halographic grating 30 (Instruments, S.A. Inc. Metuchen, N. J.), an optical transmission slit 32, an emission lens 34, a container 36, such as a glass or plastic ampule or cuvette, for containing a sample liquid or chemical 38 to be analyzed in the spectrophotometer, a source lens 40 and a light source 42. The lenses 34 and 40 are of optical quality ground glass and are of a type conventionally used in spectrophotometric instrumentation, and are commercially available from Melles Griot. The light source 42 is a xenon lamp for producing light pulses lasting approximately 2.3 microseconds, which is considerably less than the time spent by a sample in the axis of the light beam in the case of a rapid rotary analyzer e.g. with a rotor rotating at 1800 rpm. The xenon lamp is of the bulb type and has a power of about 7 W. If the energy released per flash is 0.3 joules for 2.3 microseconds, the mean power emitted during these 2.3 microseconds is equivalent to that from a 130 kW continuous xenon lamp. Clearly, there is a gain in light level and consequently in the signal/noise ratio by using a pulsed lamp like light source 42. However, as described herein, the detector assembly 10 is constructed such that these, and the other difficulties of conventional spectrophotometers previously described, are overcome or minimized, in accordance with the concepts of the invention.

In use of the detector assembly 10 in the optical system 28, light emitted from the source 42 is focused by the lens 40 through the container 36 containing the sample 38. As well known to those skilled in the art, certain constituents of the sample 38 will absorb certain wavelengths of the light emitted from the source 42, and other wavelengths will be emitted therefrom and impinge upon the lens 34. The lens 34 functions to focus such emitted wavelength of light through the slit 32 and onto the grating 30. The grating 30, in turn, disperses and reflects the light from the slit 32 which impinges thereupon to the detector assembly 10, where the intensities of light are detected and converted into electrical signals indicative of the presence and/or amount of constituents present in the sample 38, as previously described.

The components of the detector assembly 10 can be selected as follows. Preferred for use as the filters 18 are those commercially available from Hoya Optical Company. For example, the filters which have been selected for use in an especially preferred embodiment of the invention are commercially designated V-340, B-440, Y-50, Y-52 and O-56. These filters have well known optical transmission and absorbance properties. Alternatively, optical improvements can be made over the aforedescribed. If narrow band interference filters, such as those available from Microcoating Laboratories, are used in place of the previously-described "cutoff" filters; however these filters result in additional cost. The filters are, preferably, cut to a size of about 4 mm length $\times$ 0.8 mm width $\times$ 0.8 mm height, and thereafter several of such filters having the capability of passing different wavelengths therethrough (depending on which wavelengths are ultimately desired to impinge upon the individual ones of the photodiodes with which the filter assembly is to be used) are assembled together in a linear array as previously described.

The optically opaque material utilized between the filters can be, for example, a black epoxy commercially available from Epoxy Technology, Inc., Billerica, MA, under the name EPO-TEK 320. This material is described by the manufacturer as a two-component, room temperature curing, black epoxy, a 0.0005 inch thick film of which will transmit less than 0.0001% of light over a wavelength range of 300 angstroms to 1 micron. Full details of the method of use of such material to form the filter array of the invention are available from the foregoing manufacturer.

The photodiode array 12 can be any suitable commercially available array designed for use in, e.g. spectrophotometric optical systems. Especially advantageous for use in the present invention are the multi-element silicon detectors manufactured by Hamamatsu Corporation, Midlesex, N.J.

In an especially preferred embodiment of the invention, it is found to be advantageous for the reduction of electronic cross talk inside the photodiode array itself, that a non-used photodiode be present between photodiodes which are intended for signal use. This non-used, or "dummy" diode must necessarily be externally electrically shorted. The use of the shorted dummy diode can reduce electronic cross talk by a factor of approximately 500. A further reduction of cross talk can be achieved by etching deep groves around the signal diodes, as described by Kim, et al., in *Optical Engineering*, Vol. 22, No. 5, p. 656, 1983.

The following is an example of specification of a preferred detector array assembly which has been fabricated in accordance with the present invention. The example is intended to be merely illustrative of the characteristics of such a detector and to further teach how to make and use such a device, but is not to be construed as limitative of the invention in any way, the scope of which is defined solely in the appended claims.

Example
PREFERRED DETECTOR ASSEMBLY

| Filter No. | Distance from #1 Centerline | Wavelength (NM) | Hoya Filter Number |
|---|---|---|---|
| 1 | 0.000 | 340 | U-340 |
| 2 | 2.450 | 415 | B-440 |
| 3 | 3.602 | 450 | B-440 |
| 4 | 5.259 | 500 | Y-50 |
| 5 | 7.099 | 555 | Y-52 |
| 6 | 7.840 | 577 | Y-52 |
| 7 | 8.788 | 605 | O-56 |
| 8 | 9.735 | 633 | O-56 |

Physical Characteristics

Detector width 0.640 mm $\pm$ 0.025 mm.

Detector height 4.20 mm $\pm$ 0.025 mm.

No cumulative tolerances, centerline distance tolerance $\pm$ 0.025 mm.

Individual filter size 0.8 mm wide $\times$ 0.8 mm thick $\times$ 3.8 mm long, $\pm$ 0.1 mm.

Package: 16 pin standard dip, ceramic.

Electrical Characteristics

Sensitivity: Better than 0.3 A/W at 600 nm, 0.15 a/w at 350 nm, optimized at 340 nm.

Uniformity: $\pm$ 5% across any channel, $\pm$ 10% channel to channel on a single chip.

Rise time: 1 Microsecond max (330 nm to 700 nm into 50 ohms).

Cross talk: 0.005% at OV bias, 5 us pulse from 330 nm to 700 nm.

Dark Current: Less than 50 pA, at 37 degrees C. (10 mV reverse Bias).

Operating Temp: 20 degrees–50 degrees C.

Noise Current: Less than $5 \times 10^{-14}$ A (rms)/H$^{\frac{1}{2}}$ at 37 degrees C.

It is to be appreciated that according to the present invention improvements can be made in a spectrophotometer for general use, e.g., one without moving mechanical parts, and has advantages resulting from the combined use of a flash lamp and the detector previously described. By definition, however, this spectrophotometer can also be used for measuring transmission or absorbance of a wide variety of samples in a given spectral range, e.g., for conventional measurements of solutions used for clinical chemical analyses, in a static or moving cell.

What is claimed is:

1. In a spectrophotometer comprising:
   (a) a flash lamp;
   (b) a grating for receiving a beam of light delivered by the flash lamp which has passed through a sample for analysis; and
   (c) a detector situated to receive the beam of light reflected by said grating; the improvement wherein the detector comprises:
      a photodiode array assembly including:

a plurality of individual photodiodes situated in a first plane wherein a substantial portion of said photodiodes are separated one from the other by an externally electrically grounded photodiode to reduce electrical crosstalk;

a plurality of individual adjacent spectral filters situated substantially parallel to said first plane and contacting said plurality of photodiodes wherein an optically opaque material surrounds each of said spectral filters, whereby components of light are allowed to pass through one of said spectral filters to one of said individual photodiodes but said components of light are blocked, after entering said one of said filters, from passing through any other one of said filters such that light passing through each of said individual adjacent spectral filters will impinge upon only one of said individual photodiodes; and a means for attentuating stray light, said means being situated substantially parallel to said first plane and adjacent to said plurality of individual spectral filters such that said means is located above each of said individual photodiodes.

2. A method for producing a photodiode array assembly comprising the steps of:
(a) selecting a photodiode array having a plurality of individual photodiodes, each of said individual photodiodes having a preselected response to one or more wavelengths of light and separating a substantial portion of said photodiodes one from the other with an externally electrically grounded photodiode to reduce electrical crosstalk;

(b) selecting a spectral filter array having a plurality of individual adjacent spectral filters surrounded by a thin film of an optically opaque material such that each of said individual spectral filters transmits one or more preselected wavelengths of light; and (c) mounting said spectral filter array in a plane parallel to said photodiode array such that each of said individual spectral filters is contacting one of said individual photodiodes; whereby light passing through one of said individual spectral filters in said spectral filter array will impact on only one of said individual photodiodes in said photodiode array.

3. A photodiode array assembly comprising: a photodiode array comprising a plurality of photodiodes situated in a first plane wherein a substantial portion of said photodiodes are separated by an externally electrically grounded photodiodes to reduce electrical crosstalk;

a plurality of spectral filters wherein each spectral filter is surrounded by a thin film, optically opaque material and where said spectral filters are situated substantially parallel to said first plane and contacting said photodiode array, such that light passing through one of said spectral filters impacts one of said photodiodes; and means for attenuating stray light, said means being situated substantially parallel to said first plane and adjacent to said spectral filters, such that said means is located substantially over each of said photodiodes;

whereby light entering said stray light attenuating means is directed through said spectral filters to each of said photodiodes.

* * * * *